United States Patent
Park et al.

(10) Patent No.: US 11,369,737 B2
(45) Date of Patent: Jun. 28, 2022

(54) LINEARLY ACTUATED FLOW CONTROLLER FOR INTRAVENOUS (IV) FLUID ADMINISTRATION

(71) Applicant: CareFusion 303, Inc., San Diego, CA (US)

(72) Inventors: Soon Park, Cypress, CA (US); Janice Pak, Centennial, CO (US); Wesley Underwood, Yorba Linda, CA (US); Siddarth K. Shevgoor, Mission Viejo, CA (US)

(73) Assignee: CAREFUSION 303, INC., San Diego, CA (US)

( * ) Notice: Subject to any disclaimer, the term of this patent is extended or adjusted under 35 U.S.C. 154(b) by 509 days.

(21) Appl. No.: 16/359,695

(22) Filed: Mar. 20, 2019

(65) Prior Publication Data

US 2019/0290841 A1    Sep. 26, 2019

Related U.S. Application Data

(60) Provisional application No. 62/646,155, filed on Mar. 21, 2018.

(51) Int. Cl.
*A61M 5/168* (2006.01)
*A61M 39/28* (2006.01)
(Continued)

(52) U.S. Cl.
CPC ...... *A61M 5/16813* (2013.01); *A61M 5/1411* (2013.01); *A61M 5/162* (2013.01);
(Continued)

(58) Field of Classification Search
CPC .. A61M 39/286; A61M 39/287; A61M 39/28; A61M 5/16813; A61M 5/1411
See application file for complete search history.

(56) References Cited

U.S. PATENT DOCUMENTS 3,215,395 A  *  11/1965  Gorbar ............... A61M 39/286
                                                         251/6
3,650,093 A  *  3/1972   Rosenberg ........... A61M 5/165
                                                          96/6
(Continued)

FOREIGN PATENT DOCUMENTS

GB          333087          8/1930

OTHER PUBLICATIONS

International Search Report and Written Opinion for Application No. PCT/US2019/023115, dated Jun. 12, 2019, 13 pages.
(Continued)

*Primary Examiner* — Nathan R Price
*Assistant Examiner* — Tania Ismail
(74) *Attorney, Agent, or Firm* — Morgan, Lewis & Bockius LLP

(57) ABSTRACT

Flow controllers for intravenous (IV) tubing are provided. A flow controller may include first and second structural members defining a cavity therebetween for a portion of the tubing, wherein the first structural member is linearly slidable along a length of the tubing to compress at least part of the portion of the tubing to control flow of a medical fluid through the tubing. A flow controller may include a first ramped wedge structure, a second ramped wedge structure configured to slide over the first ramped wedge structure to compress a portion of the IV tubing disposed between the first ramped wedge structure and the second ramped wedge structure, a yoke having a linear slot, a wheel having a pin that is radially separated form a center of the wheel and is slidably disposed in the linear slot, and a transfer structure coupled to the yoke and the first ramped wedge structure. IV sets that include a flow controller are also provided.

21 Claims, 4 Drawing Sheets

(51) Int. Cl.
*A61M 5/14* (2006.01)
*A61M 5/165* (2006.01)
*A61M 5/162* (2006.01)
*A61M 39/22* (2006.01)

(52) U.S. Cl.
CPC .......... *A61M 5/165* (2013.01); *A61M 39/286* (2013.01); *A61M 39/287* (2013.01); *A61M 2039/224* (2013.01); *A61M 2039/226* (2013.01); *A61M 2205/7518* (2013.01)

(56) References Cited

U.S. PATENT DOCUMENTS

| | | | |
|---|---|---|---|
| 4,360,007 A | | 11/1982 | Levy et al. |
| 2009/0030378 A1 | | 1/2009 | Garcia, Jr. |
| 2009/0043253 A1 | * | 2/2009 | Podaima ................ G06Q 10/10 604/67 |

OTHER PUBLICATIONS

Chinese Office Action for Application No. 201980020645.2, dated Mar. 2, 2022, 21 pages including translation.

* cited by examiner

LINEARLY ACTUATED FLOW CONTROLLER FOR INTRAVENOUS (IV) FLUID ADMINISTRATION

CROSS-REFERENCE TO RELATED APPLICATIONS

This application claims the benefit of U.S. Provisional Patent Application No. 62/646,155 entitled "LINEARLY ACTUATED FLOW CONTROLLER FOR INTRAVENOUS (IV) FLUID ADMINISTRATION," filed on Mar. 21, 2018, the disclosure of which is hereby incorporated by reference in its entirety for all purposes.

TECHNICAL FIELD

The present disclosure generally relates to intravenous (IV) fluid administration and, in particular, relates to linearly actuated flow controllers for IV fluid administration.

BACKGROUND

Intravenous (IV) administration sets, sometimes referred to simply as IV sets, for infusion of medical fluids commonly include IV tubing for coupling a medical fluid container such as an IV bag to a patient interface such as a catheter assembly for a patient. In some scenarios, gravity infusion of the medical fluid uses the force of gravity, rather than an infusion pump, to deliver the medical fluid through the IV set. Control of the flow rate through the tubing is often provided by a roller clamp on the IV tubing. However, it can be difficult to provide a desired flow rate using a roller clamp.

SUMMARY

One or more embodiments of the disclosure provide for a flow controller for intravenous (IV) tubing. The flow controller may include first and second structural members defining a cavity therebetween for a portion of the tubing, wherein the first structural member is linearly slidable along a length of the tubing to compress at least part of the portion of the tubing to control flow of a medical fluid through the tubing.

One or more embodiments of the disclosure provide for a flow controller for intravenous (IV) tubing. The flow controller may include a first ramped wedge structure, a second ramped wedge structure configured to slide over the first ramped wedge structure to compress a portion of the IV tubing disposed between the first ramped wedge structure and the second ramped wedge structure, a yoke having a linear slot, a wheel having a pin that is radially separated form a center of the wheel and is slidably disposed in the linear slot, and a transfer structure coupled to the yoke and the first ramped wedge structure.

One or more embodiments of the disclosure provide for an intravenous (IV) set. The IV set may include a flow controller configured to be coupled to medical tubing. The flow controller may include first and second structural members that define a cavity therebetween for receiving a portion of the medical tubing, wherein the first structural member is linearly slidable relative to the second structural member, in a direction that is non-perpendicular to the second structural member, and wherein a size of the cavity is reduced as the first structural member is slid to relative to the second structural member.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

In accordance with various aspects of the subject disclosure, a clamp-style flow controller is provided. The flow controller may be an interlocked wedge-on-wedge IV tube clamp in which a pair of wedge structures form a cavity for the IV tubing and one of the wedge structures is linearly slidable along a length of the tubing to compress the tubing between the wedge structures. In some examples, to provide user continuity with the experience of operating roller clamps, while providing finer control and improved flow rate maintenance relative to a roller clamp, a rotational or rotary control structure can be included in the flow controller. The rotational control structure can be coupled to a transfer mechanism that translates the rotational motion of the rotational control structure into linear motion of one of the wedge structures.

Figure 1:
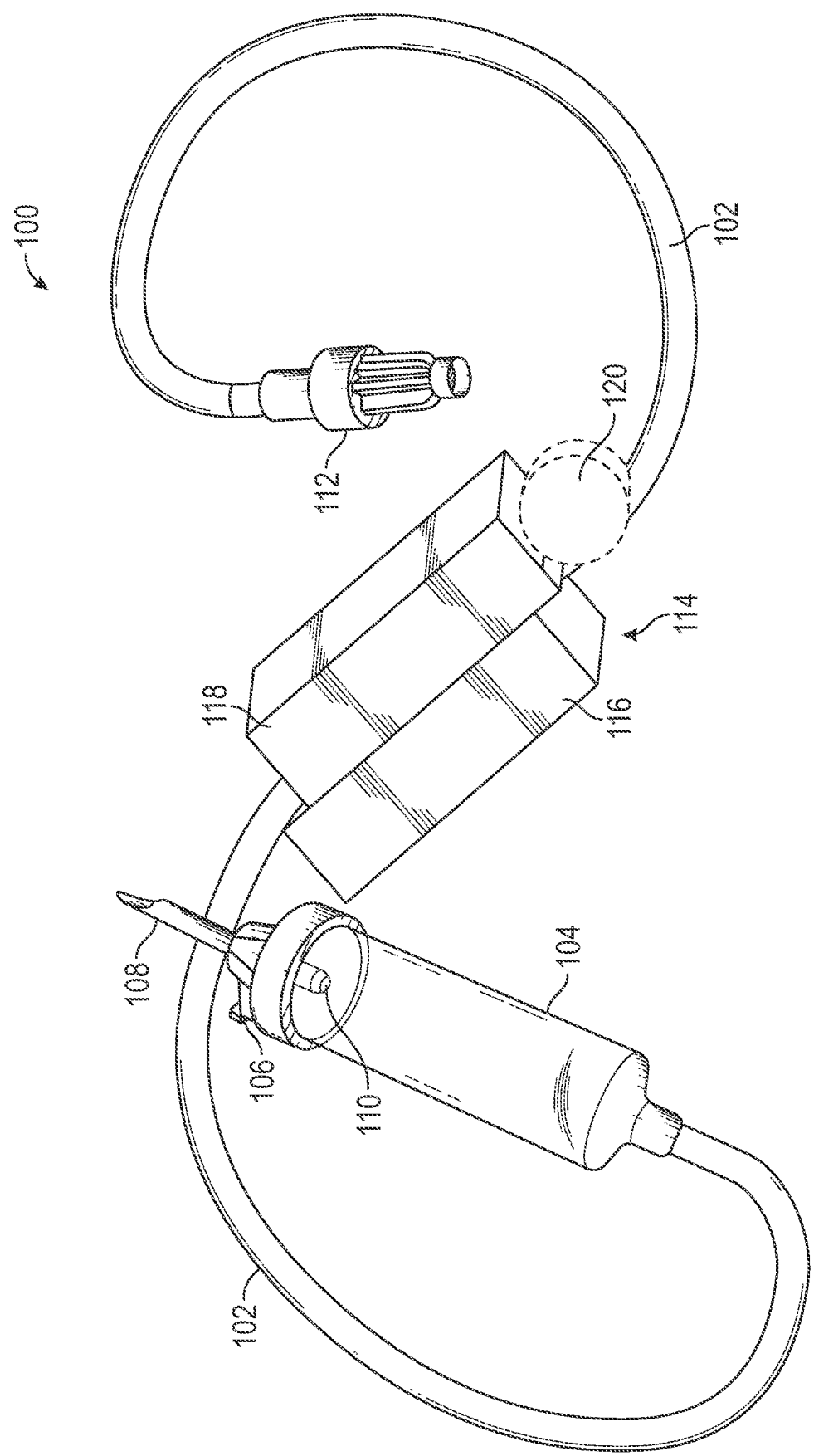
FIG. 1 is a schematic illustration of an intravenous (IV) set having flow controller according to certain aspects of the present disclosure.

FIG. 1 shows an example of an intravenous (IV) set that can include a flow controller as described herein in accordance with various examples. However, it should be appreciated that the flow controller described herein can be used with other IV sets or medical tubing.

In the example of FIG. 1, IV set 100 includes tubing 102 coupled between a connector 104 for a medical fluid container and a connector 112 for a patient interface such as a catheter assembly. Connector 104 may include a piercing spike 108 (e.g., a sharp spike for piercing rubber stoppers or a rounded and blunt spike for insertion into a bag). Piercing spike 108 may include one or more channels such as one channel for fluid and optionally a second channel for venting. Connector 104 may include a drop chamber, as shown, coupled to piercing spike 108 via drop generator 110. Connector 104 may include a vent such as vent 106 to allow air to flow into the IV fluid container. The vent may be provided with a bacterial filter to prevent bacteria from entering the IV set.

Drop generator 110 may be provided at the top of the drop chamber to allow formation of drops of medical fluid of a desired size from a connected container such as an IV bag. Drops from drop generator 110 fall into the drop chamber such that the chamber is partially filled with liquid. This prevents air bubbles from entering tubing 102. A particle filter may be provided at the lower aperture of the drop chamber.

When connector 112 is coupled to a patient interface such as a catheter, and the patient interface is attached to a patient, tubing 102 connects the drop chamber with the patient. Tubing 102 may have a length of, for example, around 150 cm and can be manufactured from a polymer material such as a polyvinyl chloride (PVC). Tubing 102 is shown shortened in FIG. 1 for clarity.

Connector 112 may be, for example, a Luer fitting for connection to corresponding patient interfaces having a standard Luer cone. Connector 112 can be fitted to a catheter assembly and/or a hypodermic needle for infusing the medical fluid into the circulatory system of a patient (e.g., into a patient's vein).

As shown in FIG. 1, IV set 100 includes flow controller 114 attached to tubing 102 at a location between connectors 104 and 112. Flow controller 114 may include structural members 116 and 118. Although not visible in FIG. 1, structural members 116 and 118 define a cavity therebetween that receives a portion of tubing 102. Structural member 118 is linearly slidable (e.g., relative to structural member 116) along a length of tubing 102 to compress at least part of the portion of the tubing 102 disposed therebetween to control flow of the medical fluid through the tubing. As shown in FIG. 1, flow controller 114 may optionally include a rotary control structure 120 (sometimes referred to as a rotary control member) that, when rotated, drives the linear sliding of structural member 118. However, this is merely illustrative and structural member 118 can be slid by a direct pressure on structural member 118 (e.g., by a user's finger).

Figure 2:
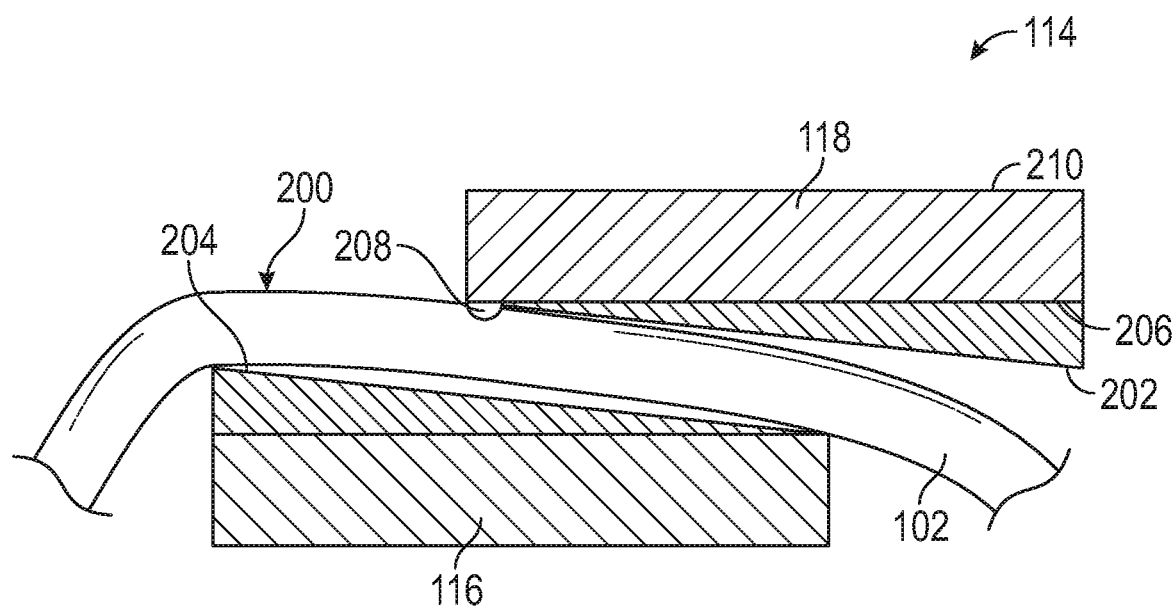
FIG. 2 illustrates a schematic cross-sectional view of a flow controller in an open configuration according to certain aspects of the present disclosure.

FIG. 2 shows a cross-sectional view of flow controller 114 in which further details of the flow controller can be seen. Structural member 118 is linearly slidable relative to structural member 116 (e.g., along a rail to which interfacing portions of both of structural members 116 and 118 are mounted). Structural member 118 may be configured to slide relative to structural member 116 in response to a pressure from a user's finger directly on an outer surface 210 of structural member or in response to a rotation of a rotary control structure such as rotary control structure 120 of FIG. 1.

Figure 3:
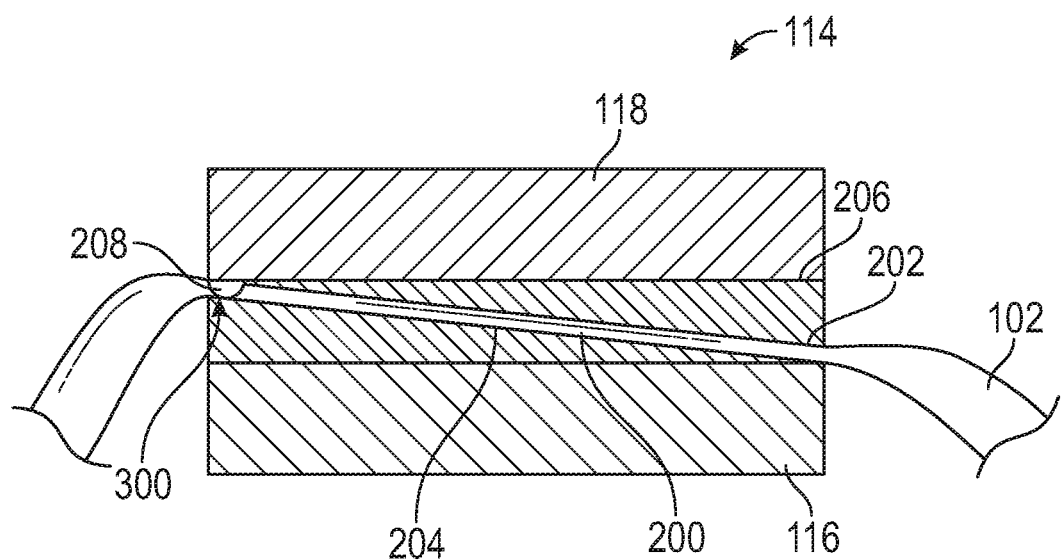
FIG. 3 illustrates a schematic cross-sectional view of the flow controller of FIG. 2 in a closed configuration according to certain aspects of the present disclosure.

In the example of FIG. 2, flow controller is shown in an open configuration in which structural member 118 is disposed in an open position in which tubing is not compressed. FIG. 3 shows a cross-sectional side view of flow controller 114 after structural member 118 has been slid linearly from the open position shown in FIG. 2 to a closed position in which portion 200 of tubing 102 is fully compressed between structural members 116 and 118 and fluid is prevented from flowing through tubing 102.

As shown in FIGS. 2 and 3, structural member 118 has a first surface that forms a portion of a cavity on a first side of tubing 102 and structural member 116 has a second surface that forms a portion of the cavity on a second side of the tubing. In the example of FIGS. 2 and 3, structural member 116 is a ramped wedge structure in which the surface of structural member 116 that contacts tubing 102 is a ramped surface 204. In the example of FIGS. 2 and 3, structural member 118 is a ramped wedge structure in which the surface of structural member 118 that contacts tubing 102 is also a ramped surface 202 that is parallel to ramped surface 204 of structural member 116 (e.g., at all positions of the linearly slidable structural member 118).

Linearly slidable structural member 118 can be moved linearly (e.g., slid) between the open position of FIG. 2, at which tubing 102 is uncompressed within the cavity between structures 116 and 118 and a closed position, linearly separated from the open position and shown in FIG. 3, in which portion 200 of tubing 102 is compressed between ramped surface 202 and ramped surface 204 to stop flow of the medical fluid through the tubing.

Linearly slidable structural member 118 is continuously slidable between the open position of FIG. 2 and the closed position of FIG. 3. Each intermediate position of linearly slidable structural member 118 between the open position and the closed position is associated with an intermediate compression of portion 200 of tubing 102 between ramped surface 202 and ramped surface 204 to set a corresponding intermediate flow rate through the tubing.

In some implementations, member 118 may have flat surface 206, rather than a ramped surface 202. In these implementations, rather than increasingly compressing substantially the entire length of portion 200 of tubing 102 between ramped surfaces 202 and 204 as structural member 118 is moved from the open position of FIG. 2 to the closed position of FIG. 3, the leading edge of structural member 118 increasingly pinches a localized part of portion 200 at or near the leading edge 300 of ramped surface 204. In another implementation, structural member 116 can be provided with a flat surface (rather than ramped surface 204) that cooperates with ramped surface 202 to compress tubing 102 at the back end of member 116 in the closed position.

In some implementations, flow controller 114 may include a third structural member. For example, a third structural member may be formed on one of surfaces 202 or 204 to reduce the friction between that surface and tubing 102 and/or between the other of surfaces 202 and 204. For example, to help ensure that tubing 102 remains stationary between structural members 116 and 118 while structural member 118 slides relative to structural member 116 to compress the tubing, surface 202 may be provided with a friction-reducing material (e.g., grease, oil, a smooth plastic slide, one or more wheels, or the like) and surface 204 may be provided with friction-increasing features such as a roughened surface or a rough-surfaced cavity interface piece between the structural member 116 and at least a portion of the cavity defined by structural members 116 and 118. In this way, flow controller 114 can be provided with low-friction on one side of tubing 102 for easy sliding, and high-friction on the other side of tubing 102 to hold the position of the tubing in the flow controller once the tubing is set.

FIGS. 2 and 3 also show how flow controller 114 can include a hard stop 208 for limiting the motion of structural member 118 relative to structural member 116. In the example of FIGS. 2 and 3, hard stop 208 includes a protrusion on ramped wedge structure 118 that contacts a corresponding portion of ramped wedge structure 116 when ramped wedge structure 118 reaches the closed position.

Hard stop 208 may be configured to limit the motion of structure 118 relative to structure 116, to provide a tactile indication that structure 118 has reached the closed position of FIG. 3, and/or to lock or hold structure 118 in the closed position until an opening force or pressure is applied. Although hard stop 208 is shown as including a protrusion on structure 118 in the example of FIGS. 2 and 3, hard stop may be provided at other locations or using other structural forms. For example, hard stop 208 may include a protrusion on structural member 116 or on or within a rotary control structure for actuating structure 118. As another example, hard stop 208 may be implemented with complementary structures on structural members 116 and 118 that interact (e.g., snap together, abut, and/or otherwise interact) to stop motion of structure 118 and to lock controller 114 in the closed configuration.

Figure 4:
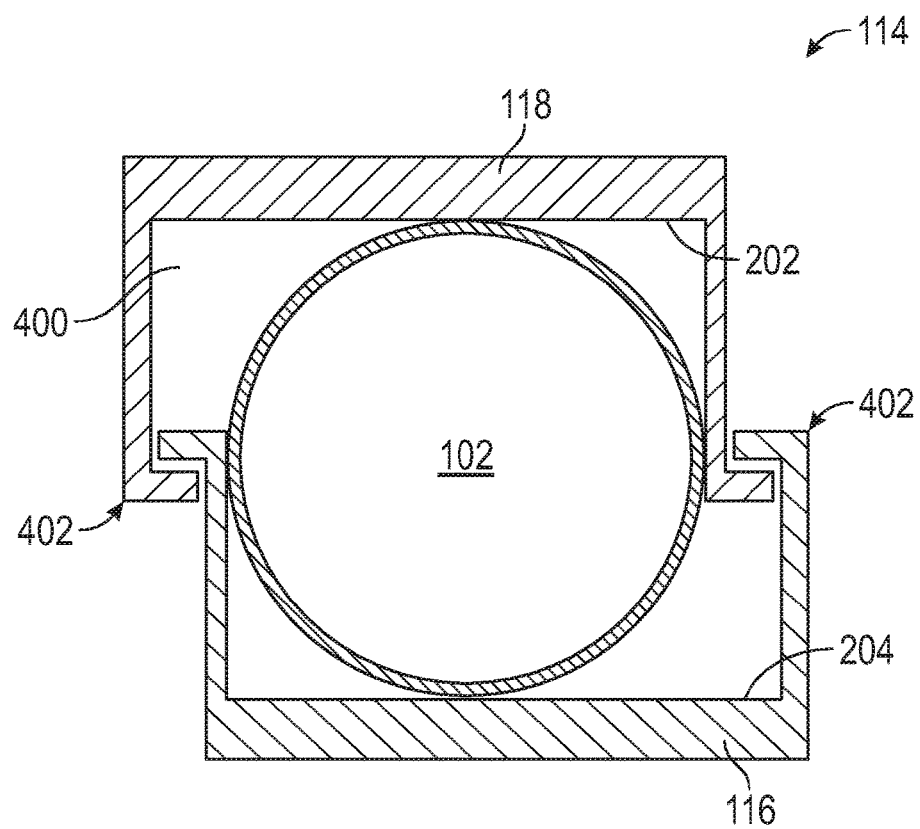
FIG. 4 illustrates a schematic cross-sectional front view of a flow controller according to certain aspects of the present disclosure.

FIG. 4 shows a face-on (e.g., front) view of flow controller 114 showing how a cavity or channel 400 for tubing 102 is formed by structural members 116 and 118. As shown in FIG. 4, structures 116 and 118 are interlocked by interlocking features 402 to create channel 400 for tubing 102 as well as keeping tubing 102 centered between structures 116 and 118. Interlocking features 402 may engage with and/or form a rail to hold and guide structural member 118 relative to structural member 116. FIG. 4 also shows how surface 202 of structural member 118 defines a portion of cavity 400 on a first side of tubing 102 and surface 204 of structural member 116 defines a portion of cavity 400 on a second side of the tubing.

As noted above, in some implementations, a rotary control member can be provided to translate rotational user-control motion into linear motion of structural member 118. Various rotational-to-linear motion conversion mechanisms can be provided, including, for example, a connecting rod mechanism, a rack and pinion mechanism, or including a scotch yoke mechanism as shown in FIG. 5.

Figure 5:
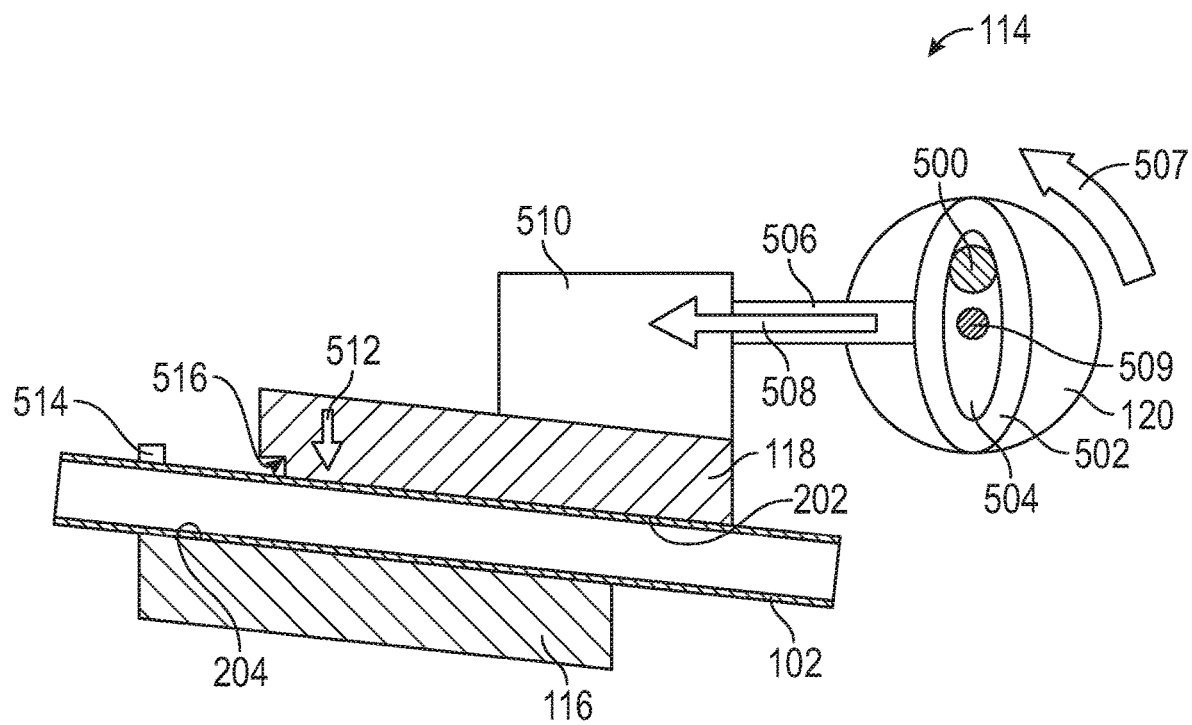
FIG. 5 illustrates a schematic cross-sectional view of a flow controller having a transfer mechanism according to certain aspects of the present disclosure.

In the example of FIG. 5, flow controller 114 includes a yoke 502 having a linear slot 504 and a wheel 120. Wheel 120 includes a pin 500 that is radially separated from center 509 of wheel 120 and is slidably disposed in linear slot 504. In the example of FIG. 5, flow controller 114 also includes a transfer structure 506 (e.g., a piston) coupled to yoke 502 at a first end and to structure 118 at a second end (e.g., directly or via an interfacing member 510).

Yoke 502 is configured to transfer rotation 507 of wheel 120 into linear actuation 508 of transfer structure 506 to linearly slide structure 118 over structure 116. The resulting linear motion of structure 118 over structure 116 causes ramp surface 202 to press downward in direction 512 on tubing 102 to compress the tubing for control of the flow of fluid therethrough.

In this way, the rotational component of the yoke mechanism can be manually actuated by a nurse or other user (e.g., using finger or a thumb) generating a linear motion within the clamp body of flow controller 114 that causes the upper wedge to slide and clamp down on the IV tubing. The linear motion generated will allow or produce flow of the IV set ranging from full, open flow of the set (e.g., as in FIG. 2) to complete occlusion of the set (e.g., as in FIG. 3).

As the slide clamp 114 reaches the closed or completely occluded position as in FIG. 3, hard stop 516 is engaged, not only providing a tactile indication that tubing 102 is now fully occluded, but also ensuring that tubing 102 stays occluded until wheel 120 is actuated in the opposite direction by the user.

Center 509 of wheel 120 may include, for example, an axle bearing with a coefficient of static friction that allows wheel 120 to hold the structure 118 in place relative to structure 116, in the absence of external force on the wheel, in any position between the open position (see, e.g., FIG. 2) and the closed position (see, e.g., FIG. 3) for structure 118. In this way, constant adjustable control of fluid flow through IV tubing 102 can be provided throughout the full range of motion of structure 118.

In the example of FIG. 5, the hard stop of flow controller 114 includes protrusion 514 on structure 116 and a corresponding recess 516 in structure 118. Hard stop structures 514 and 516 can also provide prevent flow controller 114 from drifting out of the fully occluded position. In some implementations, the hard stop for flow controller 114 is provided within the scotch yoke mechanism (e.g., to indicate and hold the structural member 118 in the closed position). In other implementations, a hard stop may be omitted and the range of motion of structural member 118 can be controlled by the shape and size of yoke 502.

Although not explicitly shown in FIG. 5, flow controller 114 may include one or more detent features between structural member 118 and linear portion 506 of the scotch yoke mechanism, the detent features providing course linear control of the position of structural member 118 and wheel 120 providing fine linear control of the position of structural member 118 between detent feature positions.

Although only a single rotational-to-linear motion conversion mechanism (e.g., wheel 120) is shown in FIG. 5, in other implementations, one or more additional rotational-to-linear motion conversion mechanisms (e.g., one or more additional scotch-yoke wheels coupled to transfer structure 506, one or more additional connecting rod mechanisms, rack and pinion mechanisms, or entirely separate additional scotch yoke mechanisms) may be provided for actuating structural member 118 relative to structural member 116. In one example, a second wheel with a larger diameter that that of wheel 120 is coupled to transfer structure 506 to provide both gross and fine linear control of the position of structural member 118. In another example, a third rotational actuator such as a rack and pinion actuator may also be coupled to structural member 118.

It should also be appreciated that, although the linear motion of transfer structure 506 has been described as imparting linear motion to structure 118, the linear motion of transfer structure 506 can, in other implementations, impart non-linear movement of structure 118 using, for example, a hinged connection to structure 118 and a non-linear guide (e.g., a ramped or curved path or rail) for the motion of structure 118. Such a non-linear guide can also be used to guide partially or completely non-linear motion of structure 118 responsive to a user's direct pressure on structure 118 (e.g., in the absence of a rotary control structure).

Figure 6:
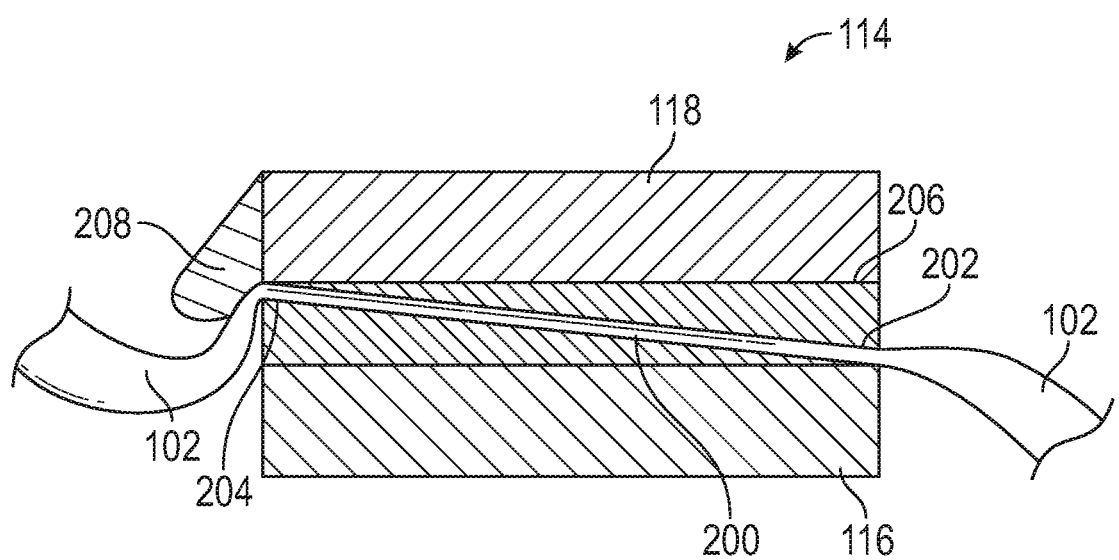
FIG. 6 illustrates a schematic cross-sectional view of the flow controller of FIG. 3 with an alternate hard stop configuration according to certain aspects of the present disclosure.

It should also be appreciated that the hard stop features of FIGS. 2, 3, and 5 are illustrative and other configurations are contemplated. For example, FIG. 6 shows an example of a flow controller 114 in which hard stop 208 is positioned in front of the leading edge of ramped surface 204. In this configuration, hard stop 208 is used to kink tube 102 to occlude the flow of medical fluid and stop the movement of structure 118, when structure 118 reaches the closed position shown in FIG. 6.

In one or more embodiments a flow controller includes first and second structural members defining a cavity therebetween for a portion of the tubing, wherein the first structural member is linearly slidable along a length of the tubing to compress at least part of the portion of the tubing to control flow of the medical fluid through the tubing.

In one or more embodiments the flow controller includes, wherein the first structural member has a first surface that defines a portion of the cavity on a first side of the tubing, the second structural member has a second surface that defines a portion of the cavity on a second side of the tubing, and wherein the second surface is a ramped surface.

In one or more embodiments the flow controller includes, wherein the first surface is a ramped surface that is parallel to the ramped second surface of the second structural member at all positions of the linearly slidable first structural member.

In one or more embodiments the flow controller includes, wherein the linearly slidable first structural member has an open position at which the tubing is uncompressed within the cavity and a closed position, linearly separated from the open position, in which the portion of the tubing is compressed between the ramped first surface and the ramped second surface to stop flow of the medical fluid through the tubing.

In one or more embodiments the flow controller includes, wherein the linearly slidable first structural member is continuously slidable between the open position and the closed position, and wherein each intermediate position of the linearly slidable first structural member between the open position and the closed position is associated with an intermediate compression of the portion of the tubing between the ramped first surface and the ramped second surface to set a corresponding intermediate flow rate through the tubing.

In one or more embodiments the flow controller includes, wherein the linearly slidable first structural member is configured to slide along a rail relative to the second structural member in response to a pressure from a user's finger on an outer surface of the first structural member.

In one or more embodiments the flow controller includes, a rotary control member coupled to the first structural member such that rotation of the rotary control member causes the first structural member to linearly slide along a rail relative to the second structural member.

In one or more embodiments the flow controller includes, wherein the rotary control member comprises a wheel for a scotch yoke mechanism coupled to the first structural member.

In one or more embodiments the flow controller includes, wherein the wheel for the scotch yoke mechanism comprises a first wheel for the scotch yoke mechanism and has a first diameter, and wherein the flow controller further comprises a second wheel having a second diameter that is larger than the first diameter to provide both gross and fine linear control of the position of the first structural member.

In one or more embodiments the flow controller includes, an additional rotational actuator coupled to the first structural member.

In one or more embodiments the flow controller includes, a plurality of detent features between the first structural member and a linear portion of the scotch yoke mechanism, the detent features providing course linear control of the position of the first structural member and the wheel providing fine linear control of the position of the first structural member between detent feature positions.

In one or more embodiments the flow controller includes, a hard stop within the scotch yoke mechanism to indicate and hold the first structural member in the closed position.

In one or more embodiments the flow controller includes, a hard stop on the second structural member to indicate and hold the first structural member in a closed position.

In one or more embodiments the flow controller is part of an IV set and the tubing is configured for conveying a medical fluid from a container to a catheter assembly.

In one or more embodiments a flow controller for intravenous (IV) tubing includes a first ramped wedge structure, a second ramped wedge structure configured to slide over the first ramped wedge structure to compress a portion of the IV tubing disposed between the first ramped wedge structure and the second ramped wedge structure, a yoke having a linear slot, a wheel having a pin that is radially separated form a center of the wheel and is slidably disposed in the linear slot, and a transfer structure coupled to the yoke and the first ramped wedge structure.

In one or more embodiments the flow controller for IV tubing also includes, wherein the yoke is configured to transfer rotation of the wheel into linear actuation of the transfer structure to linearly slide the second ramped wedge structure over the first ramped wedge structure.

In one or more embodiments the flow controller for IV tubing also includes, wherein the first ramped wedge structure has a first ramped surface, wherein the second ramped wedge structure has a second ramped surface that is parallel to the first ramped surface, and wherein a distance between the first ramped surface and the second ramped surface is controllable by the linear slide of the second ramped wedge structure to controllably compress the portion of the IV tubing.

In one or more embodiments the flow controller for IV tubing also includes, a hard stop feature on the first ramped wedge structure that limits motion of the second ramped wedge structure.

In one or more embodiments the flow controller for IV tubing also includes, an interlocking interface between the first ramped wedge structure and the second ramped wedge structure.

In one or more embodiments the flow controller for IV tubing also includes, wherein the wheel is configured to hold the second ramped wedge structure in place relative to the first ramped wedge structure, in the absence of external force on the wheel, in any position between an open position for the second ramped wedge structure and a closed position for the second ramped wedge structure for constant adjustable control of fluid flow through the IV tubing.

In one or more embodiments an intravenous (IV) set includes a flow controller configured to be coupled to medical tubing, wherein the flow controller includes first and second structural members that define a cavity therebetween for receiving a portion of the medical tubing, wherein the first structural member is linearly slidable relative to the second structural member, in a direction that is non-perpendicular to the second structural member, and wherein a size of the cavity is reduced as the first structural member is slid to relative to the second structural member.

In one or more embodiments the IV set also includes, a third structural member coupled between the cavity and one of the first or second structural member, the third structural member comprising a friction-reducing surface for at least a portion of the cavity.

In one or more embodiments the IV set also includes, a friction-increasing feature on the other of the first or second structural member.

The subject technology is illustrated, for example, according to various aspects described above. The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. Method claims may be provided to present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary and Brief Description of the Drawings are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in any claim. Rather, as the following claims reflect, inventive subject matter lies in less than all features of a single disclosed configuration or operation.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A flow controller for intravenous (IV) tubing, the flow controller comprising:
   a first structural member, comprising:
      a first outer surface; and
      a first inner surface disposed at an angle to the first outer surface;
   a second structural member, comprising:
      a second outer surface parallel to the first outer surface of the first structural member; and
      a second continuous inner surface disposed at an angle to the second outer surface and parallel to the first inner surface of the first structural member, the first and second structural members defining a cavity therebetween for a portion of the tubing; and
      a rotary control member coupled to the first structural member such that rotation of the rotary control member causes the first structural member to linearly slide along a rail relative to the second structural member,
   wherein the first structural member is linearly slidable along a length of the tubing to compress at least part of the portion of the tubing to control flow of a medical fluid through the tubing.

2. The flow controller of claim 1, wherein the first inner surface of the first structural member defines a portion of the cavity on a first side of the tubing, and the second continuous inner surface of the second structural member defines a portion of the cavity on a second side of the tubing.

3. The flow controller of claim 2, wherein the first inner surface is a ramped first surface and the second continuous inner surface is a ramped second surface, and wherein the ramped first surface is parallel to the ramped second surface at all positions of the linearly slidable first structural member relative to the second structural member.

4. The flow controller of claim 3, wherein the linearly slidable first structural member has an open position at which the tubing is uncompressed within the cavity and a closed position, linearly separated from the open position, in which the portion of the tubing is compressed between the ramped first surface and the ramped second surface to stop flow of the medical fluid through the tubing.

5. The flow controller of claim 4, wherein the linearly slidable first structural member is continuously slidable between the open position and the closed position, and wherein each intermediate position of the linearly slidable first structural member between the open position and the closed position is associated with an intermediate compression of the portion of the tubing between the ramped first surface and the ramped second surface to set a corresponding intermediate flow rate through the tubing.

6. The flow controller of claim 5, wherein the linearly slidable first structural member is configured to slide along a rail relative to the second structural member in response to a pressure from a user's finger on an outer surface of the first structural member.

7. The flow controller of claim 1, wherein the rotary control member comprises a wheel for a scotch yoke mechanism coupled to the first structural member.

8. The flow controller of claim 7, wherein the wheel for the scotch yoke mechanism comprises a first wheel for the scotch yoke mechanism and has a first diameter, and wherein the flow controller further comprises a second wheel having a second diameter that is larger than the first diameter to provide both gross and fine linear control of the position of the first structural member.

9. The flow controller of claim 8, further comprising an additional rotational actuator coupled to the first structural member.

10. The flow controller of claim 7, further comprising a plurality of detent features between the first structural member and a linear portion of the scotch yoke mechanism, the detent features providing course linear control of the position of the first structural member and the wheel providing fine linear control of the position of the first structural member between detent feature positions.

11. The flow controller of claim 7, further comprising a hard stop within the scotch yoke mechanism to indicate and hold the first structural member in the closed position.

12. The flow controller of claim 1, further comprising a hard stop on the second structural member to indicate and hold the first structural member in a closed position.

13. The flow controller of claim 1, wherein the flow controller is part of an IV set and the tubing is configured for conveying a medical fluid from a container to a catheter assembly.

14. A flow controller for intravenous (IV) tubing, the flow controller comprising:
   a first ramped wedge structure having a first inner surface and a first outer surface;
   a second ramped wedge structure having a continuous second inner surface parallel to the first inner surface and a second outer surface parallel to the first outer surface, the second ramped wedge structure configured to slide over the first ramped wedge structure to compress a portion of the IV tubing disposed between the first ramped wedge structure and the second ramped wedge structure;
   a yoke having a linear slot;
   a wheel having a pin that is radially separated form a center of the wheel and is slidably disposed in the linear slot; and
   a transfer structure coupled to the yoke and the first ramped wedge structure.

15. The flow controller of claim 14, wherein the yoke is configured to transfer rotation of the wheel into linear actuation of the transfer structure to linearly slide the second ramped wedge structure over the first ramped wedge structure.

16. The flow controller of claim 15, wherein the first inner surface is a first ramped surface, wherein the second inner surface is a second ramped surface that is parallel to the first ramped surface, and wherein a distance between the first ramped surface and the second ramped surface is controllable by the linear slide of the second ramped wedge structure to controllably compress the portion of the IV tubing.

17. The flow controller of claim 14, further comprising a hard stop feature on the first ramped wedge structure that limits motion of the second ramped wedge structure.

18. The flow controller of claim 14, further comprising an interlocking interface between the first ramped wedge structure and the second ramped wedge structure.

19. The flow controller of claim 14, wherein the wheel is configured to hold the second ramped wedge structure in place relative to the first ramped wedge structure, in the absence of external force on the wheel, in any position between an open position for the second ramped wedge structure and a closed position for the second ramped wedge structure for constant adjustable control of fluid flow through the IV tubing.

20. An intravenous (IV) set, comprising:
   a flow controller configured to be coupled to medical tubing, wherein the flow controller comprises:
   first and second structural members that define a cavity therebetween for receiving a portion of the medical tubing, the first structural member having a first continuous outer surface and a first inner surface disposed at an angle to the first outer surface, and the second structural member having a second continuous outer surface parallel to the first continuous outer surface and a second continuous inner surface parallel to the first inner surface; and
   a third structural member coupled between the cavity and one of the first or second structural member, the third structural member comprising a friction-reducing surface for at least a portion of the cavity,
   wherein the first structural member is linearly slidable relative to the second structural member, in a direction that is non-perpendicular to the second structural member, and wherein a size of the cavity is reduced as the first structural member is slid relative to the second structural member.

21. The IV set of claim 20, further comprising a friction-increasing feature on the other of the first or second structural member.

* * * * *